(12) United States Patent
Oon

(10) Patent No.: US 7,752,035 B2
(45) Date of Patent: Jul. 6, 2010

(54) METHOD, SYSTEM AND MESSAGE STRUCTURE FOR ELECTRONICALLY EXCHANGING MEDICAL INFORMATION

(76) Inventor: Yeong Kuang Oon, 29 Darryl Street, Scoresby, Victoria (AU) 3179

( * ) Notice: Subject to any disclaimer, the term of this patent is extended or adjusted under 35 U.S.C. 154(b) by 1208 days.

(21) Appl. No.: 11/299,561

(22) Filed: Dec. 12, 2005

(65) Prior Publication Data

US 2006/0136197 A1    Jun. 22, 2006

(30) Foreign Application Priority Data

| Dec. 10, 2004 | (AU) | ............................... 2004907053 |
| Mar. 30, 2005 | (AU) | ............................... 2005901531 |
| Jul. 29, 2005 | (AU) | ............................... 2005904087 |
| Oct. 25, 2005 | (AU) | ............................... 2005905894 |

(51) Int. Cl.
*G06F 17/27* (2006.01)
*G06Q 50/00* (2006.01)

(52) U.S. Cl. ............................................. 704/9; 705/2

(58) Field of Classification Search ........................ None
See application file for complete search history.

(56) References Cited

U.S. PATENT DOCUMENTS

| 5,809,476 | A  * | 9/1998 | Ryan ............................... 705/2 |
| 6,915,254 | B1 * | 7/2005 | Heinze et al. ................... 704/9 |
| 2001/0050610 | A1 * | 12/2001 | Gelston ...................... 340/5.53 |
| 2005/0119917 | A1 * | 6/2005 | Kim ............................... 705/2 |
| 2006/0004745 | A1 * | 1/2006 | Kuhn et al. ..................... 707/4 |
| 2007/0050187 | A1 * | 3/2007 | Cox ............................... 704/9 |

FOREIGN PATENT DOCUMENTS

| WO | 97/48059 A1 | 12/1997 |
| WO | 98/44432 A1 | 10/1998 |
| WO | 00/14652 A1 | 3/2000 |
| WO | 01/39037 A1 | 5/2001 |
| WO | 03/034274 A1 | 4/2003 |

* cited by examiner

*Primary Examiner*—David R Hudspeth
*Assistant Examiner*—Brian L Albertalli
(74) *Attorney, Agent, or Firm*—Christopher J. Kulish

(57) ABSTRACT

The present invention relates to a message structure for electronically exchanging medical information between applications utilizing disparate medical coding systems and record architectures, the message structure comprising an optional storyline keyword that sets the context for one or more subsequent statements, each of which statements comprise a genre selected from a set of genre keywords representing message categories, a subject, comprising either a natural language string of one or more words or a nested statement, and, optionally, one or more parametrized predicates comprising a context joiner selected from a set of context joiner keywords, and a parameter comprising a natural language string of one or more words or a nested statement.

9 Claims, 1 Drawing Sheet

METHOD, SYSTEM AND MESSAGE STRUCTURE FOR ELECTRONICALLY EXCHANGING MEDICAL INFORMATION

FIELD OF THE INVENTION

The present invention relates to a method, system and message structure for electronically exchanging medical information. In particular, the invention relates to a method, system and message structure for exchanging electronic medical records between medical record management systems each storing records that are coded according to disparate coding systems. It is also a suitable form of representation of patient health data in the life cycle of patient medical records.

BACKGROUND OF THE INVENTION

In this specification, where a document, act or item of knowledge is referred to or discussed, this reference is not an admission that the document, act or item or knowledge or any combination thereof was at the priority date:
(i) part of common general knowledge; or
(ii) known to be relevant to an attempt to solve any problem with which this specification is concerned.

The creation of a medical record for a patient is an essential aspect of medical treatment. As known by those skilled in the art, records typically include a variety of information such as doctor and nursing notes regarding the patient's complaints and symptoms, diagnoses, treatments and procedures administered, allergies, medicines the patient has been taking, medicines that are newly prescribed as well as patient demographic information.

Medical records allow physicians who treat a patient in the future to gain background regarding the patient's condition, in a continual process of storytelling and retelling that sometimes extends over a patient's entire lifetime.

Many attempts have been made to create a standardised nomenclature for diagnoses, treatments, medical procedures, medications, and other medical services for inclusion in medical records. One system is the International Classification of Diseases (ICD), which is a classification structure that provides rules for assigning numeric codes that specify diseases, injuries, the causes of these, medical findings, and other factors affecting patient care, as well as codes for surgical, diagnostic, and therapeutic procedures. Other classification systems include the Systemized Nomenclature of Medicine Clinical Terms (SNOMED CT)—which provides detailed and specific classification codes for clinical information and reference terminology, the Logical Observation Identifiers Names and Codes (LOINC)—for identifying laboratory observations—and the International Classification of Primary Care (ICPC).

The move from paper-based to fully electronic medical records has been underway for a number of years and there are many electronic medical record administration systems available. An intractable problem with these systems, however, is a lack of interoperability, being the ability of two or more systems or components to exchange information and to use the information that has been exchanged as defined by IEEE 90.

Of course, interoperability would be less of an issue if all medical data was coded into medical records using a common coding system and utilisation of a common medical record architecture, in the same manner as an ASCII file for the exchange of text. This however, is an unrealistic goal, at least at the present time. In order to ameliorate difficulties arising from the lack of interoperability, maps have been established to allow for data conversion directly from one coding system into another. In addition 'health message protocols', such as HL7 or PIT, allow for the communication of portions of medical records from one system to another by specifying the coding system in a field of the communicated data structure, with other fields of the structure populated with the requisite medical codes. Of course, the data must still be converted into the native coding system of the recipient system by utilising a conversion map (as referred to above) before it can be processed by the recipient system.

High level conversion maps are not perfect because of, amongst other things, the differing meanings captured by the codes of each system, and also because of a lack of equivalent codes between systems. This less than perfect mapping between coding systems can result in information being lost during the process of conversion. It is thus an object of the present invention to allow the exchange of medical records between systems using differing coding systems and record architectures, that reduces the likelihood of information loss occuring.

SUMMARY OF THE INVENTION

According to a first aspect of the present invention there is provided a message structure for electronically exchanging medical information between applications utilising disparate medical coding systems and record architectures, the message structure comprising an optional storyline keyword that sets the context for one or more subsequent statements, each of which statements comprise:
    a genre selected from a set of genre keywords;
    a subject, comprising either a natural language string of one or more words or a nested statement; and
    optionally, one or more parametrized predicates comprising:
        a context joiner selected from a set of context joiner keywords; and its parameter which is a natural language string of one or more words or a nested statement.

The present invention takes a different approach to that of the prior art, in that it does not attempt to provide a map directly from one coding system into another. Instead, the invention provides a message structure into which coded medical records may be easily converted for electronic exchange and conversion into another (possibly different) coded format. The non-reliance on any particular medical data coding systems will be referred to as "late binding", throughout this specification.

It will be noted that the statements of the present invention are structured as a genre-subject-predicate tuple, which is essentially a hybridized form of natural language studded with computer keywords. Indeed, medical data encoded in the statements of the present invention are quite readable by humans, as the message structure has the look and feel of natural language. Moreover, the "natural language" basis of the statements allows for very efficient conversion from a great many coding systems, because of the fact that coded electronic medical records have often been created from original 'natural language' records.

The recursive nature of the statements of the present invention (in that both a subject or a predicate may itself contain a nested statement) allow even very complex medical data to be encoded into the message structure.

The natural language basis of the structure also allows for new coding systems to be taken into account as and when they are developed.

Typically, the genre is either a medical information message or an administrative information message. Administrative messages are used for the exchange of data such as names, addresses, dates of birth and such.

Medical information messages are used to convey items of medical information and data such as: "agency" "reason for encounter" "history" "physical examination" "presentation" "diagnosis" "diagnosis+" "diagnosis~" "diagnosis−" "adverse drug reaction" "allgergy" "keep in view" "risk" "warning" "past history" "family history" "social history" "investigation" "outcome" "goal" "plan" "treatment" "no" "administration" "?" "memorandum" "mix" "problem" "immunization" "evaluation".

The optional context joiner (notated as contextJoiner) that follows the subject is a conjunctive keyword stigmatised with a colon character :. The context joiner with its adjoining natural language parameter is read together to form a predicate. One or more of these predicates working in unison further enhances the meaning and precision of the message by describing the subject. The context joiner is typically either a location descriptor, a temporal descriptor, a noun descriptor, a grammatical descriptor, an imperative descriptor or a logical descriptor.

Examples of context joiners that are location descriptors include: "about:", "above:", "across:", "aheadOf:", "along:", "among:", "associated:", "at:", "behind:", "below:", "beside:", "between:", "in:", "in FrontOf:", "into:", "near:", "nextTo:", "on:", "onto:", "over:", "toward:", of "under:".

Examples of context joiners that are temporal descriptors include: "before:", "after:", "during:", "from:", "since:", "throughout:", "while:", "until:", "for:" or "when:".

Examples of context joiners that are noun descriptors include: "complications:", "dose:", "fact:", "frequency:", "unit:".

Examples of context joiners that are imperative descriptors include: "ask:", "find:", "go:", "more:", "no:", "note:", "stop:", "start:".

Examples of context joiners that are logical descriptors are terms such as "because:", "then:", "else:" and "if:".

According to a second aspect of the present invention, interoperability in healthcare is achieved by the production and consumption of messages disclosed in the first aspect of the invention. More particularly, there is provided a method for exchanging medical information between an originating application and a recipient application, the method comprising the steps of:

converting the data to be exchanged from the data format of the originating application into one or more health information messages according to the first aspect of the invention directly or through an intermediate unitary health language;

communicating the messages in the form of the first aspect to the recipient application; and converting the messages to the data format of the recipient application by 1) the direct route, whereby the message disclosed in the first aspect is parsed directly into the format and coding system used by the recipient or 2) the intermediary route, typically the step of converting includes the steps of:

converting the data to be exchanged/received into an intermediate unitary health language; and converting the intermediate unitary health language into the first aspect message.

The intermediate unitary health language may comprise Doclescript.

The present invention is not limited to use with any particular coding system and may, for example, be used to exchange medical data between systems employing such as ICD, Docle, Read, ICPC, LOINC, or Snomed. An intermediate unitary health language such as Doclescript is useful as a "bridging" coding solution, as it has the expressivity and range of a natural language.

According to a third aspect of the present invention, there is provided a system for electronically exchanging medical information, comprising:

an originating application accessing electronic medical records comprising data coded according to a first coding system;

a recipient application communicatively coupled to the originating application via a communications network, the recipient application accessing electronic medical records comprising data coded according to a second coding system;

input means associated with the recipient application for requesting an electronic medical record from the originating application;

first converter means, associated with the originating application for converting the requested medical record to one or more health information messages according to the first aspect of the invention;

means for communicating the messages to the recipient application; and second converter means associated with the recipient application for converting the messages into an electronic medical record comprising data coded according to the second coding system.

BRIEF DESCRIPTION OF THE DRAWINGS

A preferred embodiment of the present invention will now be described by reference to the following drawings wherein.

DETAILED DESCRIPTION OF THE DRAWINGS

Figure 1:
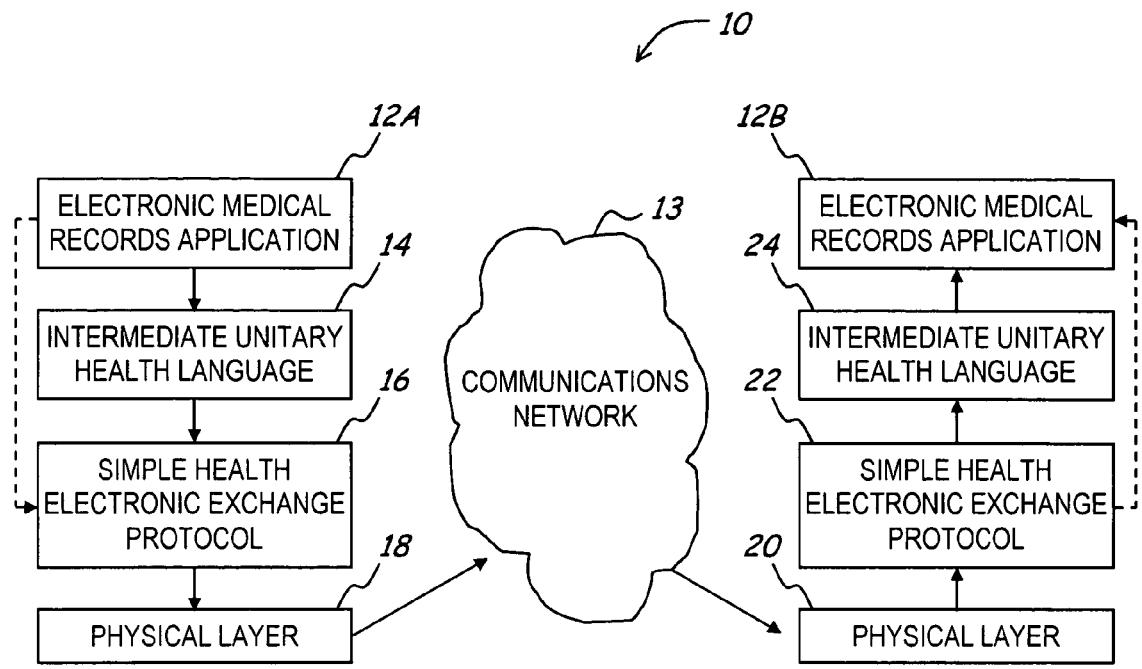
FIG. 1 is a schematic illustration of a health information exchange system and method according to the invention.

Turning to FIG. 1, a system 10 and method for exchanging health information is illustrated. Electronic medical record application systems 12A & 12B are installed and operate on separate computing platforms that are linked via a communications network 13. Each system 12A & 12B incorporates an application program and accesses a database (not shown) of electronic medical records that are encoded according to one of the known coding systems. For example, application 12A may be installed in a hospital in the United States and accesses records encoded according to the ICD classification, whereas application 12B may run at an Australian GP's office and accesses records encoded according to the ICPC classification.

In the event that application 12B requires a copy of a record that is accessible to application 12A, application 12B requests a copy through the communications network 13. On receipt of the request, application 12A extracts the record from the database and applies a conversion to it, either: through a direct route of writing out the message in Simple Health Electronic Exchange Protocol (SHEEP—see below), which can be a relatively staightforward task as each ICD numeric code has a natural language descriptor which can be used to populate the blank SHEEP messages; or through an indirect route by utilising a suitable parsing program for conversion into an Intermediate Health Language (such as Doclescript), from which it may be converted to a SHEEP.

Doclescript and its uses are more fully described in published specifications WO 97/48059, WO 98/44432, WO 00/14652, WO 01/39037 and WO 03/034274, which publications are incorporated herein by reference.

From the Intermediate Unitary Health Language 14, the data comprised in the record is converted into one or more messages 16 having a structure that is described in further detail below. Throughout this specification, this message structure will be referred to as Simple Health Electronic Exchange Protocol or SHEEP.

The SHEEP messages are then passed to the physical layer 18, where they are packed into data transport packages according to the protocols of the communications network 13. A similar physical layer 20 is present at the system 12B that accepts data packets from the communications network 13, and passes them up to the SHEEP layer 22 where the original SHEEP messages are extracted. As described in further detail below, SHEEP is a substantially natural language based protocol and is quite readable in its native format.

In turn, the SHEEP messages are passed up to the Intermediate Health Language layer 24 and then, after conversion to the coding system utilised by system 12B, into the electronic medical records application for processing and use. Alternately a parser can be constructed to parse SHEEP message directly from 22 to 12B as the natural language segments are very short (typically one to four words) and the context is fixed.

Figure 2:
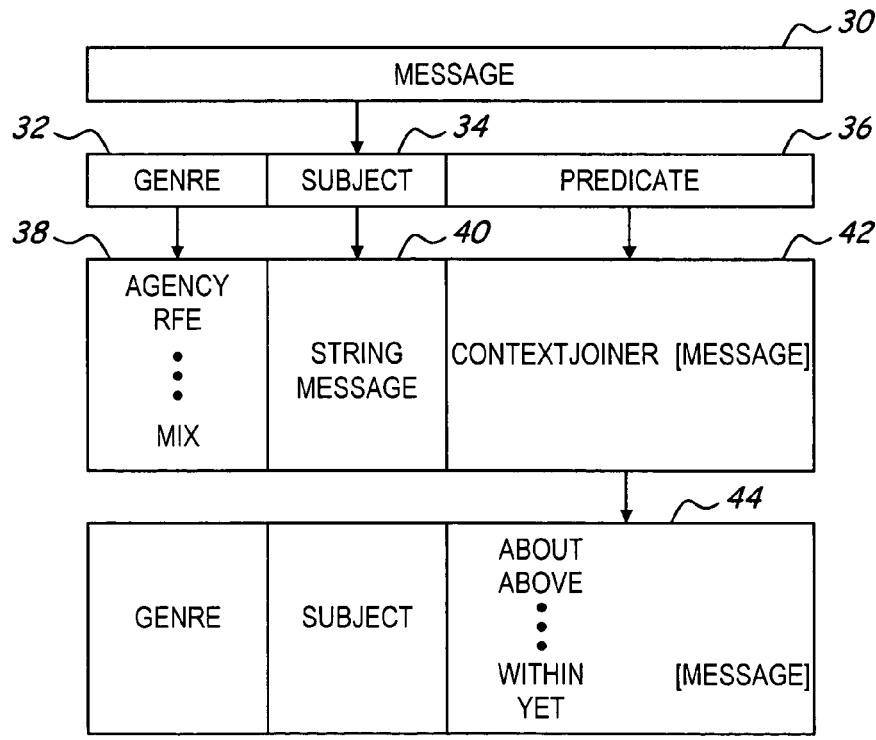
FIG. 2 is an illustration of the health information message structure according to the invention.

Turning to FIG. 2, the structure of a health information message 30 (or SHEEP message) is described in greater detail. The message 30, is made up of a genre 32, followed by a subject 34, followed by a predicate 36. As will be realized from below, the predicate is an optional component of the message.

The genre 30 is a broad description of the 'type' or 'category' of the message. The values 30 of the genre type are chosen from a list, which is described in further detail below.

The subject 34 identifies the "entity" that is the subject of the message, which is either a string of text, or a recursively defined message (ie. a genre-subject-predicate).

The predicate 36 communicates a relationship, conjunction or link between the genre and subject and its values 42 are also are selected from a list 44 of possible ContextJoiners, as described below, followed by zero or more recursively defined messages.

The full syntax for SHEEP messages is defined in Extended Backus Naur Form below.

Put another way, the following steps to output health data in SHEEP format, the word pragma means a keyword switch to guide the compiler:

i. marshalling of stored coded or uncoded health data/message into one or a series of propositions in stored memory ii. for each proposition above, the preliminary mapping to an appropriately designated SHEEP empty cast comprising of 1) genre pragmas notated in natural language 2) series of conjunctive pragmas notated in natural language iii. the SHEEP empty cast is then instantiated with the appropriate message contents by the mapping of any health codes and message contents of the proposition in step (i) into their natural language equivalents and insertion of these in the appropriate segments of the SHEEP empty cast; the subject of the proposition is inserted into the space between the genre pragma and the first conjunctive pragma; the clausal contents are inserted into their associated conjunctive pragmas to return a human and computer readable health proposition with the basic construct of genre-subject-conjunctive clause(s) in the manner of natural language expressions iv. alternately, manual construction using a text editor, of composing the propositions in step (i) into SHEEP propositions using templates of SHEEP empty casts with the subject of the proposition inserted into the space between the genre pragma and the first conjunctive pragma; the clausal contents are inserted into their associated conjunctive pragmas to return a human and computer readable health proposition with the basic construct of genre-subject-conjunctive clause(s) in the manner of natural language expressions v. the batching of SHEEP propositions into message cascade to eliminate repeating the genre with each proposition to produce a human/computer readable health message or partial/complete health record such as patient summary, discharge summary, investigation report, patient referral, clinical letter vi. the whole SHEEP message bundle is cued by the special begin ("[sh") and end ("sh]") pragmas, before it is written out, sent for further processing or sent electronically.

The following steps are utilized to process the input of health data in SHEEP format:

(a) unmarshalling of the bundle of SHEEP propositions into standalone propositions by reversing the message cascade with each SHEEP proposition having distinct genre, subject and clause segments (b) for each SHEEP proposition, the preliminary mapping to an appropriate designated empty cast of an intermediate unitary health language or equivalent construct (c) for each SHEEP proposition, the mapping of the its message contents of step (a) into health codes of an intermediate unitary health language (or an equivalent computer representational system for health data) and insertion of these codes in the appropriate segments of the propositional cast of the intermediate unitary health language to return a well formed proposition in intermediate unitary health language (d) alternate step for (c), for each SHEEP proposition, the mapping of its entire meaning content into an equivalent computer representational system for health data (e) the further mapping of the entire meaning content encapsulated in proposition of intermediate unitary health language or equivalent representation of the proposition into a single or plurality of standalone reference health codes such as SNOMED (f) the marshalling of coded computer representations above into a representation to suit local system architecture and eventual updating of local system.

Interoperability

There is a systemic interoperability taxonomy to define the level of interoperability in medical informatics:

Level 1—operates on non electronic data.

Level 2—operates on machine transportable data such as email or fax.

Level 3—operates on machine cognizable data such as structured messages, with non standard content/data; an example being display on visual display unit information from multiple sources but no integration of information Level 4—operates on machine-interpretable data with structured messages with standardized content/data; information from multiple sources are integrated and subject to electronic decision support.

This invention bypasses the above two steps. This invention obviates the need to maintain maps of one medical coding system to another medical coding system. This invention obviates the need to use a medical coding system for medical messaging as the message content is pure medical English or equivalent natural language of German or French. This invention called SHEEP for simple health electronic exchange protocol—uses a message construct that is composed of natural medical language and dynamic computer language components. SHEEP works because each medical coding system has a natural language specification of its code. SHEEP works because it defers binding to the medical codes in its embodiment. A general practitioner system that uses the Docle or ICPC coding system, can output a summary of a patient file in SHEEP message format. This patient summary in SHEEP format, which is in quite readable English state, can be imported into a hospital record system that uses ICD10Am by parsing the SHEEP message into ICD10Am using a direct parser or a Doclescript parser as a bridge. This late-binding health message structure of SHEEP is compatible with all existing and future medical coding systems as there is no specification of the medical coding used in the SHEEP message per se. SHEEP will also find green pasture incorporating new medical terminology as they are invented.

For a medical message to be sent, a medical message has to be composed according to the strict syntax of the messaging format. This message held in a medical messaging format is then packaged inside a secure email or secure electronic link to be sent to the receiver. In prior art systems, these messages are placed in a computer folder. The receiving end then needs to pick up the message held as a computer file from the computer folder, parse the medical message to extract the contents of the message to be inserted into the client medical record. The problem with prior art systems is that there is a messaging standard for pathology, there is a messaging standard for radiology, a messaging standard for patient hospital discharge to the doctor etc . This proliferation of messaging standards and for each medical subdomain creates confusion. For example, pathology laboratories use LOINC codes, general practitioners use Docle codes, while hospital discharge summaries use the ICD9 and ICD10 codes. The Tower of babel scenario where there is a proliferation of medical messaging formats using a plurality of coding systems is reality. While the holy grail appears to be a universal health messaging format utilising a universal health language, this has been merely a tantalizing goal. For that reason, medical connectivity is not happening as it should in 2004/2005. Patient healthcare is being compromised.

This invention is a unitary health messaging system to allow for data-interchange and interoperability amongst a plurality of clinical systems utilising a plurality of health coding systems and a plurality of electronic health record architectures. It does so by leveraging on the fourth layer of a new clinical information model comprising seven layers.

This fourth layer, also known as the Simple Health Electronic Exchange Protocol, is a representational system for a medical proposition comprising a hybrid of formal computer syntax segments and natural language segments.

This health messaging invention can be viewed best by looking at this 7 layered Docle health language reference model The Generic Medical Proposition Theory The generic medical proposition (GMP) theory states that a solution to the medical coding and communication conundrum in a connected health environment exists when and only when we can code for any medical proposition. The basis for this theory is that healthcare is storytelling and retelling. The basis for any story telling is the sentence or proposition.

The Docle Health Language Model

A seven layer health language model is proposed for the computer capture, representation and transmission of the medical experience that spans both intensional and extensional data. The layers are created with the following criteria: 1) the need for a different abstraction to suit a practical need 2) each layer has a different functional role from the programmatic viewpoint 3) the creation of a level to suit international protocols such as the SQL standard and the English language 4) the layers are clearly distinct and demarcated with its own dedicated syntax and grammar 5) layer boundary conditions are chosen so that information in one layer can be translated up or down, or even directly across several layers with minimal or no loss of information. The model is based on the generic medical proposition (GMP) theory which states that a solution to the medical coding and communication conundrum exists when we can code for any medical proposition.

The seven layers of the Docle health language model is described below. Analysis is given of the proximity or distance of each language level from the two endpoints of the communication chasm. This two endpoints being the mind of the human and the mind of the machine.

Late and Early Bindings of Machine Representation of Data.

A medical message is said to have "early binding" to the machine's representation of health data when actual coded health data (in say Docle, Snomed or ICPC) is sent in the message body. An alternative strategy is to send "late binding" data elements that act as proxies for the intended data send. This late binding and the use of natural language expressions as proxies for the actual message load is one of the essential components of SHEEP.

The advantages of the present invention, then, relate primarily to two related features:
  the code free, late-binding aspect of natural language messaging; and
  based on SHEEP as the point of origin in a de novo pro re nata synthesis of molecular medical codes.

As discussed above, the problem of post-coordination in medical coding has been recognized for some time. Without efficient and effective post-coordination, a system is likely to require millions of separate codes for healthcare 'story telling'.

With this in mind, the inventor has compared and contrasted Snomed CT with Docle. Docle is able comprise an endless number of codes by using combinations from a base palette of only around 20,000 atomic concepts. These atomic concepts are joined together in a process of de novo pro re nata synthesis to create molecular concepts, and this process is referred to as post-coordination.

Another way to view this process of post-coordination is to view a code for a single medical concept such as "manic depressive illness" as a gem. We are now able to cut 'facets' onto this gem to create variants. Amongst the facets applicable for "manic-depressive illness" might be, for example, the presence or absence of a past history or family history. Other facets might be the context and complex scenarios such as associating a treatment for manic-depressive illness and its outcome in the patient. The relevant Docle genus is referred to as moodDisorder^(moodd^), which has 27 species. Using the base palette of 27 concepts, we derive at least 324 useful depression codes with a plurality of retrievable and searchable facets by splicing the codes.

The Seven Layers of the Docle Health Language Model
1. there is a neurophysiological/mind state of the user that correlates with the meaning of a proposition. This is equivalent to the neurological correlate of consciousness (NCC) of Francis Crick. In mind research, Marvin Minsky call them K-lines. Medical coding activity may in the future spring from electrodes attached to the scalp. An embodiment of this layer would be a specific pattern of EEG waves. In mind research, we can examine 2 K-lines that represent the propositions: 1) "Let's try gliclazide for this patient's diabetes mellitus" and 2) "This patient has abnormal liver function tests".

2. the formal natural language layer as expressed in English, using same two examples: "I want to prescribe gliclazide for diabetes mellitus" and "The serum liver function test shows findings of abnormal elevated enzymes".

3. the informal doctor talk or Docletalk layer which captures the above 2 propositions with a minimal of keystrokes. It is terse, it will reflect regional idiosyncracies, it is doctor shorthand. It is not suited for data interoperability as it is too cryptic and fuzzy. It is suited for use as input data at the doctor desktop on the premise that the intended communicative value of the data input is reflected back to the user for confirmation:
    rx glic f diab->Did you mean "Treatment with gliclazide for diabetes mellitus"?
    xi lft f *->Did you mean "Liver function test was abnormal"?

4. The Simple Health Electronic Exchange Protocol layer (SHEEP) is the health data interoperable format. It is useful for representing the actual health message and the transport of partial and complete electronic medical records with syntactic and semantic interoperability amongst a plurality of computerized medical record systems using the same or different combinations of healthcare coding systems and health record architectures. It is a human and machine readable health domain natural language format that reads like English. SHEEP is defined in Extended Backus Naur Form; the SHEEP format is a) independent from both healthcare codes and electronic health record architectures, b) comprised of natural language expressions and natural language pragmas that act as keyword switches for the compiler. This layer is the basis of a unitary health messaging standard that transcends any formal health coding system. The two example propositions above are represented as
    [sh rx gliclazide for: diabetes mellitus sh]
    [sh ix liver function test find:abnormal sh]

while the following:
[sh language smalltalk
stub Dialog warn:'hello world'
sh]

is the SHEEP equivalent of the hello world program as the stub pragma tells the interpreter/compiler to invoke/perform the action of sending the method "warn" with parameter "hello world" to the Dialog object.

Note that there is structure. The paired square parentheses enclose one or more medical propositions.

The rx represents the treatment genre.

The "liver function test" is the subject. It is bounded by the genre and the conjunctive modifier find:. The subject is in natural language, in this instance Medical English. In the German version of SHEEP, it would of course be in German.

The context joiner or conjunctive modifier "find:" has a colon character, this is the stigma of all conjunctive modifiers.

The parameter that comes after the context joiner is in natural language, in this instance in Medical English—"abnormal".

So each SHEEP statement represents a medical proposition. The SHEEP message is enclosed in square parentheses—[sh and sh]. It has an optional storyline e.g. "patient summary" or "consultation". It has a genre, it has a subject and it has one or more joiner modifier with its parameter(s).

Another useful role of SHEEP is that of a universal medical API or application programming interface. An API is a set of definitions of the ways a computer application communicates with another computer application. It is a method of achieving commonality of abstraction level by the two communicating computer applications moving up or down its respective levels. At this SHEEP level, there is no binding to any formal health coding systems such as Snomed, ICPC, ICD9, ICD10 or Docle. Because there is no binding yet to any formal coding system, we can term SHEEP as a late binding health application programming interface(API). API saves work all round in that it provides "black box" functionality in allowing reference calls to the black box and in the implementation or re-implementation of such a "black box" API as a web service or software development kit without the breaking of the caller program. For messaging between two electronic health record architectures—the SHEEP propositions can be embedded in standard PIT and HL7 messages as a mixing component. The 3 fair assumptions being that 1) both ends talk English and messages are immediately useful 2) both ends can easily export messages in SHEEP as it is no harder than exporting a word processed document 3) SHEEP can be interpreted into an intermediate unitary health language such as Doclescript or equivalent representational system.

5. the Doclescript level, the two examples have equivalent expressions at this level—&ctx@rx[gliclazide],for[diabetesMellitus]
   &ctx@ix[s@liverFunctionTest],find[abnormal]

This is also referred to as the intermediate unitary health language (IUHL), it is a coded form of the propositions. For messaging between two electronic health record architectures—the Doclescript propositions can be embedded in standard PIT and HL7 messages as a mixing component on the optimistic assumption that both ends talk Doclescript.

6. the EHRBUS (electronic health record basic unified syntax) level is posited as the computer equivalent of the human neurological correlate of consciousness. It is also referred to the COMM(Correlate of medical messaging) layer. It is implemented as an SQL tabular structure. The EHRBUS is a generic unified container for any medical proposition. Each Doclescript proposition can be deconstructed and plugged into this EHRBUS that is defined at the SQL table level. At this level the intermediate unitary health language called Doclescript is expressed in the SQL paradigm. As a consequence, each Doclescript proposition becomes amenable to SQL manipulation. It is standardization at this level that delivers the promises of a universal open health record architecture.

7. the inferential mapping level—the implications of each proposition can be coded in ICD9, ICD10, ICPC, Snomed CT, DRG, Docle or Read coding system. An algorithm based translator to convert propositions to discrete codes is discussed. In the preferred embodiment Doclescript propositions can be reassembled from a SHEEP proposition or EHRBUS proposition. From the Doclescript representation, Docle codes can be inferred from each Doclescript proposition using prepositional logic e.g.
   &ctx@eval[diabetesMellitus],in[1995]->diabm:eval,in: 1995
   &ctx@ix[papSmear],find[abnormal]->paps:ix,find:abno Analysis of Possible Candidates in the Seven Layers of the Model from Viewpoint of Use in Messaging An effective health communication strategy is to look at the status quo of the health IT landscape with its plurality of medical record architectures/software platforms and divergent medical coding systems. With reference to the language model above, it is possible achieve level 4 interoperability in healthcare messaging utilising any one or more layers of 1) SHEEP layer 2) Doclescript layer or 3) EHRBUS layer. This invention seeks to solve the current health communication problems of multi-record architectures, multi-health coding environments by not interfering with the users ultimate choice of health coding representational system and its idiosyncratic record architecture/software platform. By taking this stance, it is future proofing this health messaging system and it is not locked onto any existing or yet-to-be-invented health coding system. This late binding approach is suited for an environment when we are still groping for a unified health language. In the scenario where everyone uses the same or similar word based health coding system then layers 5 (Doclescript—where there is early binding) or 6 (ehrbus—where there is pre-emptive binding in the sense that the sender of the message knows about the SQL tabular data structure to insert the data) would be ideal for health messaging.

The author initially looked at attacking the problem at another location in the communication chain. The choice location being the computer memory that represents the correlate of medical messaging. The example below clarifies this point.

It is conjectural and plausible that the states of mind of a French, German, Chinese, Japanese, Korean or English speaking physician reading a patient summary with a sentence, in their respective languages, such as "This patient has carcinoma of the lung associated with 40 year history of heavy cigarette consumption"—will evoke very similar firing of patterns of neuronal activity at roughly the same brain loci. This pattern of neuronal activity in the brain can be said to be the neurological correlates of the sentence. It is postulated that there is an underlying neuronal pattern language in healthcare that is at its substratum layer that is common to healthcare expressed in any language . . . be it French, German, Chinese, Japanese, Korean or English. This is backed up by the experiments of neurologist William Penfold, who electrically stimulated different areas of the brain of a patient to evoke intense experiences in the patient. Artists have the knack for expressing timeless truths as evidenced by the quote by songwriter Jesse Harris "One flight down" sung by Norah Jones—"One flight down, there's a song on low. And it's been there playing all along. Now you know. Now you know." This invention of messaging with SHEEP recognizes that there is this "song on low", that is one flight down from SHEEP there is Doclescript. Another flight down from Doclescript there is EHRBUS. So in effect there are two lower "roads" in the medical messaging worlds below SHEEP—the "high road" SHEEP can be mixed in with the traditional health messaging protocols such as PIT and HL7. When the SHEEP road is more travelled, then the less travelled road of Doclescript and EHRBUS may be explored. At the lowest of the "low roads" where medical messaging is reduced to exchanging gestalts between the memories of two computer systems using EHRBUS.

EHRBUS

In a previous invention by the inventor, a unified table structure for patient transactions were posited—and transportability was achieved by sending Doclescript health messages or Doclescript messages encased in PIT or HL7. In prior art, these propositions expressed in Doclescript was parsed and posted to the end user medical record system. In the prior art the users of Doclescript would need a Doclescript parser to parse the Doclescript messages. Whereas in this invention it obviates the need for the user to parse Doclescript as it is already "pre-digested". One way of clarifying this EHRBUS way is to use the "Experiencing tasting of ice-cream example". Tasting of the ice-cream can be effected by actually ingesting the ice cream. The cold sensation in the mouth and associated anatomical structures, the stimulation of the taste and smell receptors create a neurological correlate of consciousness in the brain that equates to "tasting the ice cream". Supposing we have a precise map of the neurological correlates of "tasting the ice cream" and the resources to recreate this map of the neurological correlates of consciousness in the brain—we do not need real physical ice cream to evoke the "tasting the ice cream" experience if we can get to the end of the messaging chain directly by whatever means. We can have a delectable ice cream experience using the logical equivalent of wiring up the patient to evoke EEG activity to simulate the satiety and gustatory centres and an infusion pump to the vein to release the equivalent sugar, flavours, carbohydrate, protein and lipid nutrients. This invention does exactly that by creating the maps for the end point of the medical messaging chain. The maps are based only in part on the Doclescript medical language (see PCT/au00/01460, pct/au02/1422).

Doclescript medical language (see PCT/au00/01460, pct/au02/1422).

Underlying Theories

The philosophical undergirding of SHEEP is based on the following principles:
English syntax and grammar
object oriented messaging
conventional medical language as used in the real world.

The SHEEP Parser

The SHEEP parser enables conversion from a Sheep message to Docle script statements.

The SHEEP message is parsed into a Doclescript statement by the steps of:
removal of begin and end square parentheses;
slicing the SHEEP statement string into a dictionary with key value pairs for the genre, the subject and each context joiner;
selection of an empty doclescript cast to conform to the SHEEP statement;
parsing the value of each key of dictionary into Docle equivalent concept representation; and
populating the empty cast of the doclescript statement.

The operation of the SHEEP Parser can be demonstrated for a SHEEP message conveying the information that an individual has had diabetes mellitus for 2 years:
'[sh eval diabetes mellitus for: 2 years sh]'
The dictionary with the following key-value pairs are generated:('for'->'2 years' 'cast'->'&ctx@eval[ ],for[ ]' 'theme'->'diabetes mellitus' 'genre'->'&ctx@eval')
The empty cast &ctx@eval[ ],for[ ] is populated by the coded concepts:
diabetesMellitus
Ideally, results are exported in SHEEP
[sh eval diabetes mellitus for: 2 years sh]->
Docdescript expression: &ctx@dx@+[diabetesMellitus]
EXPRESSION CAST: &ctx@dx@+[ ]
Expression CAST IN English: add this diagnosis/these diagnoses to list
Molecular Docle codes: diabm:dx@+

Atomic Docle codes: diabm dx@+
Atomic ICPC: NA
Molecular ICPC: NA
Atomic ICD10AM: 132342
Molecular ICD10AM
Molecular SNOMED: 98575757
Atomic SNOMED: 144141 523535

The Simple Health Electronic Exchange Protocol (SHEEP) defined in EBNF.

The present invention relates to a message structure called SHEEP for electronically exchanging medical information between applications utilising disparate medical coding systems. The message structure comprises a hybrid of computer keywords and natural language segments, an optional storyline keyword that sets the context for the following one or more statements, which comprise:

a genre selected from a set of genre keywords;
a subject, comprising either a natural language string of one or more words or a nested statement; and
optionally, one or more parametrized predicates comprising:
  a context joiner selected from a set of context joiner keywords; and its parameter which is a natural language string of one or more words or a nested statement.

The above ideas are presented in a more mathematic notation below. The language definition of SHEEP is based on Extended Backus Naur Formalism (EBNF is discussed in 'Programming in Modula 2' by Niklaus Wirth, Springer-Verlag, 1982).

The EBNF Syntax rules are defined as:
Syntax={rule}.
rule=identifier "=" expression ".".
expression=term {"|" term}.
term=factor {factor}.
factor=identifier|string|"(" expression ")"|"[" expression "]"|"{" expression "}".

The SHEEP Language is a sequence of syntax rules.
The right hand of each rule defines syntax based on previous rules and terminal symbols.
Parentheses ( ) group alternate terms.
The vertical bar | separates alternate terms.
Square brackets [ ] denote optional expressions.
Braces { } denote expressions that may occur zero or more times.

A medicalExpression is a generally accepted medical expression in natural language. In the examples English is used.
DocleWordSeparator:=",","|",";".
DocleOperators="!"|"<"|">"|"%"|"@"|"#"|"$"|"%"|"^"|"&"|"*"|",".
letter=capitalLetter
  |"a"|"b"|"c"|"d"|"e"|"f"|"g"|"h"|"i"|"j"|"k"|"l"|"m"|"n"
  |"o"|"p"|"q"|"r"|"s"|"t"|"u"|"v"|"w"|"x"|"y"|"z".
capitalLetter="A"|"B"|"C"|"D"|"E"|"F"|"G"|"H"|"I"|"J"|
  "K"|"L"|"M"|"N"|"O"|"P"|"Q"|"R"|"S"|"T"|"U"|"V"|
  "W"|"X"|"Y"|"Z".
digit="0"|"1"|"2"|"3"|"4"|"5"|"6"|"7"|"8"|"9".
nextLine=cr|lf|crlf.
character=letter|digit|DocleOperator.
word={character}.
comment=""{word}"".
medicalExpression=word {" "word}|bleat.
medicalExpressionSeries=medicalExpression {";" medicalExpression} contextjoiner="about:"|"above:"|"across:"|"after:"|"against:"|"aheadOf:"|"along:"|"although:"|"among:"|"and:"|"around:"|"as:"|"ask:"|"asso:"|"at:"|"auth:"|"bcos:"|"behind:"|"below:"|"before:"|"beside:"|"between:"|"but:"|"by:"|"comx"|"coda:"|"csdr:"|"ctx:"|"date:"|"dateEvent"|"dose:"|"down:"|"during:"|"except:"|"fact:"|"find:"|"for:"|"freq:"|"from:"|"go:"|"how:"|"if:"|"in:"|"is:"|"inFrontOf:"|"insteadOf:"|"into:"|"ix:"|"like:"|"more:"|"no:"|"not:"|"near:"|"nextTo:"|"not:"|"note:"|"of:"|"on:"|"onto:"|"original:"|"outx:"|"over:"|"pack:"|"qty:"|"rpt:"|"sans:"|"start:"|"stop:"|"since:"|"that:"|"though:"|"thru:"|"throughout:"|"tn:"|"to:"|"toward:"|"under:"|"unit:"|"unless:"|"until:"|"up:"|"val:"|"when:"|"whether:"|"while:"|"who:"|"why:"|"with:"|"within:"|"yet:"|"then:"|"else:".

genreAbbreviated="agency"|"rfe"|"hx"|"px"|"hxpx"|"dx"|"dx+"|"dx~"|"dx-"|"adr"|"allg"|"kiv"|"risk"|"warn"|"phx"|"fh"|"sh"|"ix"|"outx"|"goal"|"plan"|"tx"|"no"|"admn"|"?"|"memo"|"mix"|"prob"|"immx"|"eval".

genreNonAbbreviated="agency"|"reason for encounter"|"history"|"physical examination"|"presentation"|"diagnosis"|"diagnosis+"|"diagnosis~"|"diagnosis-"|"adverse drug reaction"|"allgergy"|"keep in view"|"risk"|"warning"|"past history"|"family history"|"social history"|"investigation"|"outcome"|"goal"|"plan"|"treatment"|"no"|"administration"|"?"|"memorandum"|"mix"|"problem"|"immunization"|"evaluation".

genreAbbreviated="agency"|"rfe"|"hx"|"px"|"hxpx"|"dx"|"dx+"|"dx~"|"dx-"|"adr"|"allg"|"kiv"|"risk"|"warn"|"phx"|"fh"|"sh"|"ix"|"outx"|"goal"|"plan"|"tx"|"no"|"admn"|"?"|"memo"|"mix"|"eval".

storyline="patient summary"|"consulation"|"lab report"|"radiology report"|"hospital discharge"|"referral"|"consultant report"|"record dump"|"medication list"|"prescription"|"language"
genre=genreAbbreviated|genreNonAbbreviated
subject=medicalExpressionSeries.
predicate=contextJoiner [medicalExpression|medicalExpressionSeries].
simpleStatement=subject{predicate}{comment}.
statement=genre simpleStatement.
compoundStatement=genre{nextLine simpleStatement}.
bleat=statement|compoundStatement
sheep=("["|"s"|"[sh")[storyline]bleat|{bleat}("]"|"s]"|"sh]")

Explanatory Notes:
  The term comx means complications.
  The term csdr means consider.
  The term bcos means because.

Examples of Sheep Messages
  In the following examples the message is firstly given in natural text (English in this instance) followed by SHEEP. A SHEEP message is also referred to as a bleat for a single statement message and bleatBleat for a multi-statement SHEEP message.
  Message category for reason for encounter.
  Reason for encounter of skin laceration.

[rfe laceration skin]
  Reasons for encounter of cough, feeling depressed.

[rfe feeling depressed; cough]
  Reason for encounter of cough for 3 weeks

[rfe cough for:3/52]
  Reason for encounter of epilepsy for 2 hours
[rfe epilepsy for:2/24]
  Message category for clinical history.
  History of cough.
[hx cough]
  History of cough for 2 days.
[hx cough for:2/7]
  History of no cough
[hx cough ctx:no]
  History of cough in 2002
[hx cough in:2002]
  History of cough, diarrhoea and weight loss.
[hx cough;diarrhoea;weight loss]
  Message category for physical examination.
  Physical finding of inguinal lump.
[px inguinal lump]
  Physical finding of inguinal lump 10 cm.
[px inguinal lump val:10 unit:cm]
  Physical examination chest finding of pigmented skin lesion.
[px chest find:pigmented skin lesion]
  Physical examination found no raised jugular venous pressure.
[hx jvp find:normnal]
  Physical examination found raised jugular venous pressure.
[hx jvp find:abnornal,high]
  Physical examination found raised jugular venous pressure 4 cm.
[hx jvp find:abnormal,high val:4 unit:cm]
  Physical examination of skin found no petechiae.
[px skin find:petechiae ctx:no]
  Physical examination found no petechiae.
[px petechiae ctx:no]
  Message category for diagnoses and problem lists.
  Diagnosis of diabetes mellitus.
[dx diabetes mellitus]
  Add diagnosis of diabetes mellitus to your active problem list.
[dx+diabetes mellitus]
  Add diagnosis of diabetes mellitus diagnosed in 2001 to your active problem list.
[dx+ diabetes mellitus in:2001]
  Remove diagnosis of acute appendicitis from your active problem list.
[dx− acute appendicitis]
  Oops. Change diagnosis of acute appendicitis to Crohn's disease in active problem list.
[dx~ acute appendicitis to: Crohn's disease]
  Add diagnoses of diabetes mellitus, chronic renal failure, gout,alopecia to your active problem list.
[dx+ diabetes mellitus; chronic renal failure;gout;alopecia]
  Active problem list of diabetes mellitus, ischemic heart disease,tia.
[dx@heap diabetes mellitus; ischemic heart disease;tia]
  No known diagnosis of diabetes mellitus in this patient.
[dx diabetes mellitus ctx:no]
  Undiagnosed weight loss.
[udx weight loss]
  Undiagnosed weight loss of 6 months.
[udx weight loss for 6/12]
  Differential diagnoses of tuberculosis and sarcoidosis.
[ddx tuberculosis; sarcoidosis]
  Keep in view possibility of deep vein thrombosis.
[kiv deep vein thrombosis]
  Risk of suicide.
[risk suicide]
  Risk of acute renal failure; metabolic acidosis.
[risk arf; metabolic acidosis]
  Message category for drug related propositions.
  Treat bronchitis with amoxil brand of amoxicillin
[rx amoxicillin tn: amoxil for:bronchitis]
  Treat bronchitis with augmentin (augmentin is mixture of amoxicillin and clavulanate).
  This is an example of the recursive nature of bleat.
[rx [mix amoxil; clavulanate] for:bronchitis]
  Treat diabetes mellitus with gliclazide on active medication list
[rx+gliclazide for:diabetes mellitus]
  Drug treatment captopril.
[rx captopril]
  Start drug captopril on 17 jul 2004.
[rx captopril start:17 jul 2004]
  top captopril on 12/7/2005.
[rx captopril stop:12/7/2005]
  Stop captopril because of cough in 2002.
[rx captopril stop:2002 bcos:cough]
  Patient responding, happy with Drug treatment with captopril.
[rx captopril outx: ☺]
  Patient responding, happy with Drug treatment with captopril for hypertension.
[rx captopril for:hypertension outx: ☺]
  Patient started on Drug treatment with captopril for hypertension in 2003.
[rx captopril for:hypertension start:2003]
  Drug dosing regime of amoxicillin of amoxil brand, 250 mg capsule one every 8 hours after meals for 7 days.
[rx amoxicillin tn:amoxil dose:250 mg form:capsule qty:1 freq:8/24 for:7/7 more: after meal]
  Drug script of amoxicillin of amoxil brand, 250 mg capsule one every 8 hours, pack 20.
[rx amoxicillin tn:amoxil dose:250 mg form:capsule qty:1 freq:8/24 pack:20]
  Mixture of clavulanate and amoxicillin.
[mix amoxicillin;clavulanate]
  Message category for procedural treatment related propositions.
  Appendectomy for acute appendicitis.
[tx appendectomy for: acute appendicitis]
  Cryotherapy for plantar warts.

[tx cryotherapy for: warts plantar]
  Stop cryotherapy treatment for plantar warts because of infection in 2005.

[tx for: warts plantar stop: 2005 bcos: infection]
  Stop iv feed treatment for coma because of brain death in 2002.

[tx iv feeding for: coma stop: 2002 bcos: brain death]
  Message category for outcomes and complications.
  "post for post op"
  Patient with deep vein thrombosis after abdominal aortic surgery day 14.

[dx aaa surgery comx: dvt at:14/7]
  The isomeric equivalent of above being:

[dx dvt from: aaa surgery at: 14/7]

or equally good is

[outx deep vein thrombosis post: abdominal aortic surgery]
  Message category for allergies, adverse drug reactions and warnings.
  Allergic to amoxicyllin

[alig amoxicyllin]
  Allergic to amoxicyllin, erythromycin and tegretol

[allg amoxicyllin; erythromycin; tegretol]
  Allergic to amoxicyllin to give rash

[alig amoxicyllin to:rash]
  Allergic to peanuts to give anaphylactic shock.

[alig peanut to:anaphylactic shock] . . . leads to associate message of

[dx+ anaphylactic shock from:peanut]
  Adverse reaction to carbamazepine.

[adr carbamazepine]
  Adverse reaction to carbamazepine, dilantin, augmentin.

[adr carbamazepine;augmentin;dilantin]
  Adverse reaction to carbamazepine to give diarrhoea.

[adr carbamazepine to:diarrhoea]
  Warning, this patient a codeine abuser.

[warn codeine abuse]
  Warning, this patient a substance abuser.

[warn substance abuse]
  Machine tagged warning. This example shows a proposition inside another proposition.

[warn@ai [adr warfarin; aspirin to: increased inr]]

(aGenre='genre@eval') ifTrue:[^#('&ctx@dx[ ]'&ctx@dx[ ],with[ ]'&ctx@dx[ ],with[ ],to[ ]'&ctx@dx[ ],sans [ ]'&ctx@dx[ ],to[ ]'&ctx@dx[ ],from[ ]'&ctx@dx[ ],ctx [ ]'&ctx@ddx[ ]'&ctx@ddx[ ],val[ ]'&ctx@risk@of [ ]'&ctx@risk@of[ ],val[ ]'&ctx@kiv[ ]'&ctx@kiv[ ],for [ ]'&ctx@udx[ ]'&ctx@udx[ ],for[ ]'&ctx@udx[ ],ctx [ ]'&ctx@ddx@ai[ ]'&ctx@drug@allg@+[ ],to [ ]'&ctx@drug@adr@+[ ],to[ ]'&ctx@eval [ ]'&ctx@warn[ ],ctx[ ]'&ctx@warn@ai[ ]')].
  Message category for past medical history.
  Past history of tuberculosis.

[phx tuberculosis]
  Past history of tuberculosis in 1979.

[phx tuberculosis in:1979]
  No past history of tuberculosis.

[phx tuberculosis ctx:no]
  Past history of tuberculosis, myocardiac infarction, typhoid.

[phx tuberculosis; myocardiac infarction; typhoid]
  Message category for family medical history.
  Family history of tuberculosis.

[fh tuberculosis]
  No family history of tuberculosis.

[fh tuberculosis ctx:no]
  Family history of tuberculosis, myocardiac infarction, typhoid.

[fh tuberculosis; myocardiac infarction; typhoid]
  Message category for social history.
  Social history of unemployment.

[sh unemployment] or [shx unemployed]
  No social history of gambling.

[sh gambling ctx:no]
  Social history of smoking 20 cigarettes per day.

[sh smoking val:20]
  Social history of smoking 20 cigarettes per day starting in 1975.

[sh smoking start:1975 val:20]
  Social history of smoking 20 stopping in 1977.

[sh smoking stop:1977]
  Social history of smoking starting in 1975 and stopping in 1988.

[sh smoking start: 1975 stop: 1988]
  Social history of 5 standard alcoholic drinks per day.

[sh drink val:5]
  Social history of 5 standard alcoholic drinks per week.

[sh drink val:5 freq:1/52]
  Social history of having stopped alcoholic drinks in 1999.

[shgstop drink in: 1999]
  Social history of tennis, golf, fishing.

[sh tennis;golf;fishing]
  Played tennis for 10 years.

[sh tennis for:10/1]
  Started tennis for in 1981.

[sh tennis in:1981]
  Message category regarding iatrogenic harm minimization
  Do not use magnetic resonance imaging on this patient.

[no mri]
  This patient has no allergies

[no allergy]
  Do not give eggs or peanuts to this patient.

[no egg;peanut]
  Please do not give me penicillin, bactrim or erythromycin

[no bactrim;penicillin;erythromycin]
  Do not use magnetic resonance imaging on this patient because of pacemaker.

[no mri bcos:pacemaker]
  Please do not give me penicillin, bactrim or erythromycin or even think about using mri on me.

[no bactrim;penicillin;erythromycin;mri]
  Message category regarding administrative data.
  Patient surname is oon

[admn surname is: oon]
Patient firstname is yeong

[admn firstname is: yeong]
Patient street is 29 darryl st

[admn street is: 29 darryl st]
Patient suburb is Scoresby

[admn suburb is: Scoresby]
Patient state is Victoria

[admn state is: Victoria]
Patient country is Australia

[admn country is: Australia]
Patient email is Docle@compuserve.com

[admn email is: Docle@compuserve.com]
Patient id is 23232332

[admn id is: 23232332]
Patient cupid is kit19874d@thean@han@yong39.56n32.52e

[admn cupid is: kit19874d@thean@han@yong39.56n32.52e]
Message category for memoranda and recall
Recall this patient in 2 months

[memo self in:2/12]
Recall this patient in 2 months by email

[memo self in:2/12 by:email]
Recall this patient in 2 months by phone

[memo self in:2/12 by:phone]
Remind the doctor to this patient's case in 2 months by email

[memo dr in:2/12 by:email]
Message category for goal and planning.
Goal for diabetes mellitus control is hba1c of <6.5.

[goal diabeteMellitus with:hba1c is:<6.5]
Goal for inr control for dvt is between 2 and 2.5

[goal dvt with:inr from:2.0 to:2.5]
(aGenre='genre@goal') ifTrue:[^#('&ctx@mx@goal
[ ]''&ctx@mx@goal[ ],val[ ],unit[ ]''&ctx@mx@goal
[ ],val[ ],unit[ ],for[ ]''&ctx@mx@goal[ ],find
[ ]''&ctx@mx@goal[ ],find[ ],for[ ]')].

(aGenre='genre@goal') ifTrue:[^#('&ctx@mx@goal
[ ],with[ ],val[ ],unit[ ]''&ctx@mx@goal[ ],with[ ],find[ ]')].
Message category for planning messages.
Plan for managing hypertension by reviewing patient every 2 weeks.

[plan hypertension with:consult freq:2/52]
Plan for managing diabetes mellitus by doing hba1c every 4 weeks.

[plan diabetes mellitus with:hba1c freq:4/52]
Message category for outcome messages.
Outcome of treatment of diabetes mellitus with gliclazide, patient feels better.

[outx diabetes mellitus outx:better with:gliclazide]
Outcome of treatment of diabetes mellitus with metformin, patient feels worse.

[outx diabetes mellitus outx:worse with:metformin]
Patient is feeling much worse with his depression.

[outx depression outx:much worse]
Patient is cured with respect to his depression.

[outx depression outx:cure]

Exploring Post-SHEEP-messaging Using Doclescript and EHRBUS.

The SHEEP invention paves the way forward for more sophisticated health messaging using direct mapping of a message between two computer system memories, creating gestalts to correlate with the form and meaning of the message in respective computer memories, without the need for marshalling and unmarshalling the medical message in and out of a health language transport layer This messaging by exchanging EHRBUS "gestalts" between computer memories can also lead to the reconstruction of the original message as an intermediate health language such as Doclescript. Medical messaging by exchanging gestalts posits a "start" and an "end" point which are correlates of medical messaging which are represented by read/write access to a time-stamped series of repeated pre-designated named memory locations and meaning switches in each of the user's computer; whereby an instance of such a series represents a medical message and each of the named memory locations of such an instance has a specific contextual meaning that is contingent upon the values of a generic meaning switch and/or specific meaning switches, generating a message amenable to computer algorithm processing to derive canonical clinical codes, and a message that is a gestalt of the a) meaning of the named locations, b) the values in said named locations and c) the values of the meaning switches; and contained in any one instance of the series, a meta-message pertaining to the medical message, which is stored in a pre-designated named location; this meta-message informs the receiver about the recommended course of action to be taken about said medical message, and is expressed as programmatic method stubs and their parameters to provide the linkage for execution by the receiver of its own versions of such programmatic methods on specified parameters.

The Problem of Health Messaging

Healthcare is storytelling and retelling. Messages need to be passed amongst providers of health care and the patients themselves for collaborative problem solving over a time line that may exceed a couple of decades. Hitherto messages written in English held in paper records suffice, but not so in the computer era where there is a proliferation of data often held in computer databases. There exists also the tantalising prospect that the machine can help the medical care process itself with timely machine decision support. This is particularly true in the era of patient held electronic health records in the background of increased patient awareness and participation in their own health management. To derive maximum benefit from computerised health messaging, these health messages need to be in a structured and coded format to make them computer readable and amenable to computer processing. Health connectivity is dependent on sending and receiving of medical messages. Currently these medical messages are sent in HL7 (health language 7) or PIT formats. Typically prior art systems depend heavily on marked up languages like SGML/XML.

For a medical message to be sent, a medical message has to be composed according to the strict syntax of the messaging format. This message held in a medical messaging format is then packaged inside a secure email or secure electronic link to be sent to the receiver. In prior art systems, these messages are placed in a computer folder. The receiving end then needs to pick up the message held as a computer file from the computer folder, parse the medical message to extract the contents of the message to be inserted into the client medical record. The problem with prior art systems is that there is a messaging standard for pathology, there is a messaging standard for radiology, a messaging standard for patient hospital discharge to the doctor etc . This proliferation of messaging standards and for each medical subdomain creates confusion. For example, pathology laboratories use LOINC codes, general practitioners use Docle codes, while hospital discharge summaries use the ICD9 and ICD10 codes. The Tower of babel scenario where there is a proliferation of medical messaging formats using a plurality of coding systems is reality. While the holy grail appears to be a universal health messaging format utilising a universal health language, this is merely a tantalising goal. For that reason, medical connectivity is not happening as it should in 2004/2005. Patient healthcare is being compromised.

Processing and Storing SHEEP Messages

The SHEEP invention alleviates the health messaging problem in all its aspects of the invention described. SHEEP also paves the way for deeper and more efficient way for two computer systems to communicate, in particular the delights of communicating at the EHRBUS(COMM) level is discussed. The preferred embodiment of processing and storing SHEEP messages is their conversion to doclscript and then held in SQL tables of the COMM type(Correlate of Medical Messaging). COMM represents the common denominator end of the medical messaging chain. System vendors of medical software can feed of COMM using SQL query language. The target goal is to create an instance of COMM for each medical message received. With the SHEEP framework, COMM SQL tables is the natural fit for storing the parsed message in COMM (EHRBUS) format. Messaging can be effected by direct manipulation at the COMM level. For security purposes, any data inserted or changes to the COMM tables has to be effected by programs sanctioned and stored on the machine at the receiving end of the messaging—see PHP program example. In this example the php script resides on the receiving end. This script is invoked by an outside php script and passes the SQL instruction as a parameter. Similarly in another embodiment, a web service on the client side, a SOAP or XMLRPC service can be invoked to update the COMM. In summary the centurion guards are actually programs that reside on the receiver side; this guards the sanctity of the data. In one embodiment, a SHEEP medical message is received, it is parsed into Doclescript, this is then parsed into a Sql statement that caused a row to be added to a COMM arrival table. The quickest way to achieve an addition of a row to the COMM table is through communication of an industry standard SQL statement. In this post SHEEP processing, one good endpoint of medical communication is effected by inserting/updating of a COMM table. Practice with SHEEP messages makes likely future medical messaging based on Doclescript or mere exchange of SQL statements to update COMM tables at both ends.

Any system and method of medical messaging is based on a system where there is total elimination of the medical messaging format layer may have to wait. Medical messaging that is attained by creating changes termed COMM (correlate of medical message) in the computer system is demonstrated in the following pages. Typically, this correlate of medical message (COMM is represented by a row in a unified structured query language (SQL) table. This correlate of medical message (COMM) is the possible ideal outcome if a medical message had been sent in a pre-agreed medical message format and its contents parsed and data posted. A preferred embodiment of this invention has each node in a messaging network a 1) SEND correlate of medical message (SEND COMM) and a 2) RECEIVE correlate of medical message (RECEIVE COMM). COMM (correlate of medical message) is structured for direct query by client applications and hence ready for immediate inter-operability by client systems. This system obviates the complexity of assembly of and sending of such a medical message in any given medical messaging format. This system obviates the complexity of receiving, parsing and posting of data of such a medical message received in any medical messaging format.

In one embodiment of COMM(EHRBUS) communication there exists a http server, sql service and a server side scripting language like PHP or Microsoft ASP or even a WEB service like soap or XMLRPC.

A poor man's implementation of COMM is just a SQL service with the COMM tables.

A poorer man's implementation of his medical record is a SQL dump of his COMM tables, this serves as his medical record backup.

COMM is converting a medical messaging problem into a SQL programming problem.

Detailed Description of the ARRIVAL COMM table:

```
'CREATE TABLE arrival
(transactId      int(11) NOT NULL AUTO_INCREMENT
                 PRIMARY KEY,
patientid        varchar(64)    NOT NULL   ,
cpid             varchar(128)       ,
sender           varchar(128)       ,
addressee        varchar(128)          ,
cc        varchar(128)       ,
ack       varchar(128)       ,
initials         varchar(24)                    ,
dateentry        date      NOT NULL
                 ,
on_              datetime      NOT NULL
                 ,
genre            varchar(60)                    ,
code             varchar(60)                    ,
transacttype     varchar(255)                       ,
Doclescript      text                       ,
ask              varchar(128)                   ,
with_      varchar(128)                ,
to_              varchar(128)                    ,
from_            varchar(128)                    ,
who                   varchar(128)
                 ,
bcos                  varchar(128)
                 ,
at_              varchar(128)                    ,
theme            text                        ,
find             varchar(128)                    ,
sans             varchar(128)                    ,
for_             varchar(128)                    ,
ctx              varchar(128)                    ,
fact             varchar(128)                    ,
go_              varchar(128)                    ,
stop             varchar(128)                    ,
outx             varchar(128)                        ,
val              varchar(128)                    ,
unit             varchar(128)                    ,
dose             varchar(128)                    ,
pack             varchar(128)                    ,
tn               varchar(128)                    ,
form             varchar(24)                     ,
qty              varchar(24)                     ,
more             varchar(24)                     ,
freq             varchar(128)                    ,
rpt              varchar(128)                    ,
blo              blob                        ,
```

-continued

```
dx          text            ,
hxpx        text            ,
xi          text            ,
tx          text            ,
ix          text            ,
tamt        text            ,
note        text            ,
text        text            ,
stub        text            ,
auth        varchar(32)     ,
coda        varchar(128)
) TYPE = InnoDB;'
```

The DEPARTURE COMM Table Specifications:

```
'CREATE TABLE departure
(transactId    int(11) NOT NULL AUTO_INCREMENT
               PRIMARY KEY,
patientid      varchar(64)  NOT NULL  ,
cpid           varchar(128)        ,
sender         varchar(128)        ,
addressee      varchar(128)        ,
cc             varchar(128)        ,
ack            varchar(128)        ,
initials       varchar(24)         ,
dateentry      date    NOT NULL    ,
on_            datetime  NOT NULL  ,
genre          varchar(60)         ,
code           varchar(60)         ,
transacttype   varchar(255)        ,
Doclescript    text                ,
ask            varchar(128)        ,
with_          varchar(128)        ,
to_            varchar(128)        ,
from_          varchar(128)        ,
who            varchar(128)        ,
bcos           varchar(128)        ,
at_            varchar(128)        ,
theme          text                ,
find           varchar(128)        ,
sans           varchar(128)        ,
for_           varchar(128)        ,
ctx            varchar(128)        ,
fact           varchar(128)        ,
go_            varchar(128)        ,
stop           varchar(128)        ,
outx           varchar(128)        ,
val            varchar(128)        ,
unit           varchar(128)        ,
dose           varchar(128)        ,
pack           varchar(128)        ,
tn             varchar(128)        ,
form           varchar(24)         ,
qty            varchar(24)         ,
more           varchar(24)         ,
freq           varchar(128)        ,
rpt            varchar(128)        ,
blo            blob                ,
dx             text                ,
hxpx           text                ,
xi             text                ,
tx             text                ,
ix             text                ,
tamt           text                ,
note           text                ,
text           text                ,
stub           text                ,
auth           varchar(32)         ,
coda           varchar(128)
) TYPE = InnoDB;'
```

System and Method of Operation

The example below is given of a patient initiated consultation on the web. The web application collects a history. At the end of the web consultation a record of the consultaion needs to be created of this consultation for future review by patient of the healthcare professional. In one embodiment, the client has a http server and a SQL service running on her computer or USB stick. A script e.g. in PHP on the patient machine is invoked with the SQL instruction as parameter is invoked and the ARRIVAL COMM table in patient held record is updated.

The method stub of message tells what methods to invoke by the receiver, the parameters are provided. In this example the stub holds the values:

hxpx@+(cough@chronic:for%2/52,seek@view)

Insert Into Arrival (dx,on_,code text,xi,theme,patientId,DocleScript,dateEntry, transactType,tamt,genre,tx,ix,stub) VALUES(" ","2004/10/29","Docle",
"@text"," ","@theme","oyk","&ctx@hxpx@ai [cough@chronic:for%2/52,seek@view;wheezing:no; cough@nocturnal:for%4/12;chestsensitive:no;chest@pain: no;chest@pain|antacid:no;chest@pain|lean@forward; chest@pain%hr],xi [ ],dx[ ],tx[ ],ix[ ],tamt[.chest],text [Main complaint(s):cough chronic for 2 week(s), History: no wheezing cough nocturnal for 4 month(s) no chest sensitive no chest pain no chest pain|antacid chest pain|lean forward chest pain
hrDifferential_diagnosis:   inflammation.periCardiumasthmaasthma/
infectionasthma@exerciseasthma@statusasthma@ allergymyocardialInfarctionmyocardialInfarction@antero LateralmyocardialInfarction@inFeriormyocardial Infarction@
subendocardialTo_ask:
wheezingchest@pain>arm@leftchest@pain%hrchest@ painchest@pain@anteriorchest@pain@leftchest@pain> jawsweat*hcough@chronicnauseavomitingback@pain@ thorax]","2004/10/29","&ctx@hxpx@ai[ ],xi[ ],dx[ ], tx[ ],ix[ ],tamt[ ],text[ ]",".chest","hxpx"," "," ","hxpx@+ (cough@chronic:for%2/52,seek@view)")

The method stub of message tells what methods to invike by the receiver, the parameters are provided. In this example the stub holds the values:

hxpx@+(cough@chronic:for%2/52,seek@view)

The method or procedure call has the name hxpx@+ which means history/examination (presentation) of chronic cough for 2 weeks and it is an active problem for the patient and sums up the message in a nutshell The method stub of message tells what methods to invoke by the receiver, the parameters are provided. In this example the stub holds the values:

dx@+(diabetesMellitus)

The method or procedure call has the name dx@+ which means diagnosis of diabetes mellitus and it is an active problem for the patient, please add to the problem list. The message stub sums up the message in a nutshell in a procedure call with parameters format.

We can have multiple procedure calls in one message stub, the methods are separated by a ~ character. Note that the parameters in each method call is separated by the ; character e.g.:

hxpx@+(cough@chronic:for%2/52,seek@view)~dx@+
(diabetesMellitus)

Coding terminology independence:

In the COMM field/SQL table for the messaging correlates there is a field called code:

In this instance the messaging is done in Docle. It could have been in ICPC, ICD or SNOMED or READ codes. This code is one of those specific meaning switches that alters the gestalt of the message.

Callback and responses to callback (backcall) system and method:

The message stub is also the basis of a callback mechanism between two parties. For example the breast screen facility reports a mammogram as normal and leaves a message for the doctor that in the event that breast carcinoma is diagnosed they wish to be informed.

In this instance the message stub would contain the method:

callback(carcinoma.breastwww.breastscreen/callback/report_carcinoma.breast.php)

The receiver would place this stub in its callback section.

In the event that carcinoma is detected it will trigger the stub method and send a message to www.breastscreen/callback/report_carcinoma.breast.php with a message with the following stub to append to the rest of the message:

backcall(carcinoma.breast;patient_id)

The breastscreen facility will acknowledge the message from the clinic and process the backcall method appropriately.

This message stub facility allows an open ended framework for notification and exchanging of directives in a clear way.

This message stub facility allows an open ended framework for notification and exchanging of directives in a clear way, such as reporting of adverse drug reactions.

The server script on the client side expressed in PHP is:

```php
<?php
//BindEvents Method @1-B0B3AF9C
function BindEvents( )
{
 global $NewRecord1;
 global $CCSEvents;
 $NewRecord1->ehrbussql->CCSEvents["BeforeShow"] =
 "NewRecord1_ehrbussql_BeforeShow";
 $NewRecord1->TextBox1->CCSEvents["BeforeShow"] =
 "NewRecord1_TextBox1_BeforeShow";
 $NewRecord1->theme->CCSEvents["BeforeShow"] =
 "NewRecord1_theme_BeforeShow";
 $CCSEvents["BeforeShow"] = "Page_BeforeShow";
}
//End BindEvents Method
//NewRecord1_ehrbussql_BeforeShow @3-5B9FB54E
function NewRecord1_ehrbussql_BeforeShow( )
{
 $NewRecord1_ehrbussql_BeforeShow = true;
 //End NewRecord1_ehrbussql_BeforeShow
 //Custom Code @7-FF3FD3DA
 // -------------------------
  global $NewRecord1;
  // Write your own code here.
 // -------------------------
 //echo ("hello kuang 21 oct 04 ") ;
 //$sql = $_GET['ehrbussql'] ;
 $sql = $_REQUEST['anmswerDoclescript'] ;
 $ssql = $_REQUEST['answerDoclescript'] ;
 $ehrbussql = $_REQUEST['ehrbussql'] ;
 $ehrbussql = stripslashes ($ehrbussql) ;
 $theTextProper = getText( $ehrbussql) ;
 $theThemeProper = getTheme( $ehrbussql) ;
 $ehrbussql = str_replace("@text", $theTextProper, $ehrbussql ) ;
```

-continued

```php
 $ehrbussql = str_replace("@theme", $theThemeProper, $ehrbussql ) ;
 $NewRecord1->ehrbussql->setValue($ehrbussql) ;
 //echo ($sql ) ;
 //echo ($ssql) ;
 // ** to replace @theme and @text
 //$theTheme = getTheTheme($ehrbussql );
 //End Custom Code
 $host = "localhost";
 $user = "root";
 $password = "georgegeorge";
 $connection = mysql_connect($host, $user, $password)
           or die("could not connect mysql") ;
           $db = mysql_select_db("stillpoint", $connection)
               or die("db select error") ;
 $ehrbussql = stripslashes ($ehrbussql) ;
 $result = mysql_query($ehrbussql)
           or die("error in query".$ehrbussql) ;
           mysql_close($connection) ;
 //Close NewRecord1_ehrbussql_BeforeShow @3-1ED83A4B
 return $NewRecord1_ehrbussql_BeforeShow;
}
//End Close NewRecord1_ehrbussql_BeforeShow
//NewRecord1_TextBox1_BeforeShow @11-2FEC38CD
function NewRecord1_TextBox1_BeforeShow( )
{
 $NewRecord1_TextBox1_BeforeShow = true;
 //End NewRecord1_TextBox1_BeforeShow
 //Custom Code @12-FF3FD3DA
 // -------------------------
  global $NewRecord1;
  // Write your own code here.
    $theText = getText( $_REQUEST['ehrbussql'] ) ;
 $NewRecord1->TextBox1->setValue($theText) ;
 // -------------------------
 //End Custom Code
 //Close NewRecord1_TextBox1_BeforeShow @11-74544E0D
 return $NewRecord1_TextBox1_BeforeShow;
}
//End Close NewRecord1_TextBox1_BeforeShow
//NewRecord1_theme_BeforeShow @8-059A78D1
function NewRecord1_theme_BeforeShow( )
{
 $NewRecord1_theme_BeforeShow = true;
 //End NewRecord1_theme_BeforeShow
 //Custom Code @9-FF3FD3DA
 // -------------------------
  global $NewRecord1;
    $theTheme = getTheme( $_REQUEST['ehrbussql'] ) ;
 $NewRecord1->theme->setValue($theTheme);
  // Write your own code here.
 // -------------------------
 //End Custom Code
 //Close NewRecord1_theme_BeforeShow @8-DCB91505
 return $NewRecord1_theme_BeforeShow;
}
//End Close NewRecord1_theme_BeforeShow
//Page_BeforeShow @1-D8BD2467
function Page_BeforeShow( )
{
 $Page_BeforeShow = true;
 //End Page_BeforeShow
 //Custom Code @13-D5F267D7
 // -------------------------
  global $ehrbuslocal;
  // Write your own code here.
 // -------------------------
 //End Custom Code
 //Close Page_BeforeShow @1-4BC230CD
 return $Page_BeforeShow;
}
//End Close Page_BeforeShow
// Docle string functions
function getHxpx ( $str )
           { $pieces = explode(",hxpx[",$str ) ;
           // pieces[1] is the tail
           $result= explode("],xi[",$pieces[1]) ;
                 return $result[0] ;
           }
function getHxpxButLast1( $str )
```

-continued

```
// chest@pain;abdomen@pain;head@pain -> chest@pain;abdomen@pain
        { $location = strrpos($str, ";") ;
          if ( $location === false) { return "" ; }
            if ( $location == 0 ) { return $str ; }
          return substr( $str,0,$location) ;
        }
function translateHxpxToIxQuery( $str )
// &ctx@?[hxpx],hxpx[chest@pain] -> &ctx@?[ix],hxpx[chest@pain]
        {
          return str_replace("&ctx@?[hxpx]", "&ctx@?[ix]", $str) ;
        }
function translateIxToHxpxQuery( $astr )
// &ctx@?[hxpx],hxpx[chest@pain] -> &ctx@?[ix],hxpx[chest@pain]
        {
          return str_replace("&ctx@?[ix]", "&ctx@?[hxpx]", $astr) ;
        }
function get_ip( ) {
    global $HTTP_X_FORWARDED_FOR, $REMOTE_ADDR ;
    if ( !isset($HTTP_X_FORWARDED_FOR)) {
    $ip = $REMOTE_ADDR ;
                                                         }
                            else { $ip =
$HTTP_X_FORWARDED_FOR;
                                                         }
    return $ip ;
        }
function getTheme( $str ) {
                $pieces = explode("&ctx@hxpx@ai[",$str ) ;
                $result= explode("]",$pieces[1]) ;
//      $resultStr ="pieces-0:".($pieces[0])."pieces-1:".($pieces[1])."result-
    0".($result[0])."result-
1".($result[1]) ;
    return $result[0] ;
        }
function getText( $str ) {
                $pieces = explode("&ctx@hxpx@ai[",$str ) ;
                $result= explode(",text[",$pieces[1]) ;
                $tmp = $result[1] ;
                $result= explode("]",$tmp) ;
    return $result[0] ;
        }
?>
```

To invoke the script we use the command:
ehrbuslocal.php?ehrbuslocal=$the_SQL_Command Where the $the_SQL_Command is the example Insert statement given above.

In the preferred embodiment, all stakeholders (medical service providers and consumers and other government or third parties) in the medical connectivity stakes has each their ARRIVAL and DEPARTURE COMM and equipped with a HTTP/HTTPs server and SQL service. In one embodiment, the HTTP server and the SQL service is loaded onto a machine with a permanent internet connection so that medical messaging can be done at any time.

In one embodiment, the SQL service handling the arrival COMM table is fully protected against all instrusions and can only be accessed or updated based on preloaded and configured scripts on the receiving side.

In one embodiment, suitable for patient held records and mobile doctors, the HTTP server and the SQL service and equipped with the ARRIVAL and DEPARTURE COMMS is packed into a USB flash stick (typically >256 MB) so that medical messaging can be done on the go whenever there is an internet connection.

The Post-coordination Algorithm

The present invention additionally relates to a system and method of post-coordinating coded concepts, through the use of canonical standalone codes to capture full meaning. Ideally, such a code will be derived from Doclescript propositions.

A SHEEP message is passed through a SHEEP Parser to derive Doclescript proposition(s), which are then fed to a post-cordination algorithm to derive canonical standalone codes that captures the entire meaning of the proposition(s).

This section deals with the algorithmic derivation of canonical standalone codes from a Docle script propositions. Such canonical codes are termed Docle codes. Such standalone codes are used in clinical systems for matching/retrieval and in clinical decision support. How can we leverage a natural language "front" like SHEEP into a post-coordinated medical coding system? A post-coordinated medical coding system (e.g. Docle) has typically a base of 10,000 to 20,000 coded concepts; such a system has a syntax and grammar that allows the formation of billions of combinations of base concepts (post-coordination) to unleash unlimited expression/expressivity of clinical scenarios and yet generate codes that are amenable to computer searching, matching, comparison, analysis and retrieval. An algorithmic method is disclosed to arrive at standalone codes, starting from a natural language message such as SHEEP. Generating canonical standalone codes is akin to the concept of reduction in chemistry or refactoring in mathematics.

From SHEEP to Standalone Canonical Forms:

An example is to code for "plantar wart treated with cryotherapy".

The SHEEP message is: [sh rx cryoTherapy for:plantar wart with: sh]

After being parsed to Doclescript: &ctx@rx [ppoc@cryoTherapy],for[wart@plan-tar]

The post-coordinator algorithm converts the above Doclescript to the standalone canonical codes:
wart@plantar:rx,with:ppoc@cryot
ppoc@cryot:rx,for:wart@plantar In general, then, the conversion of Docle script propositions to canonical standalone codes comprises the following steps:
  conversion of Docle script into an abbreviated form using an abbreviating Docle algorithm;
  moving the Docle script subject to the front of the statement without parentheses;
  concatenating a colon character as a descriptor operator;
  concatenating the genre; and
  for each predicate:
    concatenating a comma operator, the context joiner and the parameter of the context joiner without parentheses.

Referring to the algorithm above, we start with a Docle script statement that concerns a patient's weight loss for 2 months: &ctx@hxpx[weight@loss],for[2/12]

The Docle abbreviating algorithm will produce:&ctxhxpx [weig@loss],for[2/12], giving the following canonical forms: weig@loss:hxpx,for:2/12

The construction of such standalone codes with the subject (the thematic concept) as the leading term and separator characters of colon form : allows for easy splicing and dicing of codes for in depth analysism, searching and processing.

Turning to the reverse process, the unpacking of canonical standalone codes to SHEEP messages using a reversed post-coordination algorithm:

The canonical standalone codes (an example is weig@loss:hxpx,for:2/12) contain the germ for ready regeneration back to a SHEEP message.

The algorithm comprises the steps of:
  splicing the predicates of the canonical standalone codes as denoted by the first comma of code read from the front of the code;

setting up, for each predicate, a key value pair of a context joiner and its parametric value;

splicing the genre as denoted by first colon reading from the front of the code;

looking up natural language expressions for genre and subject;

looking up a natural language expression for each parametric value of each context joiner;

assemblng the genre and the subject and appending one or more predicates comprising context joiner and its natural language expression value; and enclosing the resulting statement in square parentheses.

As an example, referring to the algorithm above, we start with a standalone canonical code (representing 'weight loss for 2 months') of weig@loss:hxpx,for:2/12, giving the following Sheep form:

[sh presentation weight loss for: 2 months sh]

The reverse post-coordination algorithm means that medical coding and messaging are seamlessly connected in the following linguistic stack: Sheep->doclescript->canonical standalone code. The leverage of such a solution is that germ of medical messaging is captured in the compacted form of a highly computable standalone canonical form.

Glossary

Docle (Docle script)—a human readable health coding system. It is based on primary and secondary keys, such as "diabetesMellitus", which maps to a secondary Docle code ("diabm") using an abbreviating Docle algorithm. The Docle algorithm returns the first four characters for a single word source, and for a two-word source, returns the first four characters of the first word concatenated to the first character of second word. For three or more word sources, it returns the first character of each word concatenated together. Tertiary keys, or aliases, are then mapped to the primary and secondary keys.

Pragmas are compiler directives. The word pragma is a short form of "pragmatic information". They comprise keyword data representing significant comments embedded in source code by programmers in order to instruct compilers about compilation.

COMM—correlate of computer messaging, used interchangeably with the EHRBUS concept.

Arrival—the COMM for all incoming messages

Departure—the COMM for all outgoing messages

EHRBUS—the SQL database that holds the arrival and departure tables.

SHEEP—an acronymn for Simple Health Electronic Exchange Protocol (also referred to as Summary Health—English Exchange Pattern). A system and method for up to level 4 interoperable health messaging using natural language expressions.

SOMR—"summer" summary oriented medical recording

Appendix

Sample Patient Summary in SHEEP messaging format:
'[sh
Patient Summary
Admn
version is: 1.0;
author is: Dr Y K Oon;
date is: 12/8/2005;
surname is:Oon;
firstname admn is:Yeong;
birthday is: 18/7/59;
Allergies
penicillin to:anaphylaxis;
erythromycin to:hives;
Adverse Drug Reactions
diabex to:diarrhoea;
Problems
diabetes mellitus in:1987;
hypertension in:2001;
dvt in:1997;
cough for:2/12;
fracture femur—right, complicated,compound type;
?tb;
travel vaccination—vietnam, thailand,india;
chest pains—undiagnosed;
Risks
ihd—high from:smoking,obesity;
carcinoma colon—high from:polyposis coli,family history;
Past History
appendectomy in:1988
brain injury—mca in:2001;
Family History
carcinoma colon—mother;
ihd—father;
polyposis coli—brother;
Social History
electrician—self employed
Medications
diamicron tn:diamicron mr dose:30 mg qty:1 freq:12/24 for:diabetes;
atorvastatin tn:lipitor dose:20 mg qty:1 freq:1/7 for:hypercholesterolemia;
Immunizations
tetanus with:tetanus toxoid tn:tetToxBrand on: 12/7/1998;
measles mumps rubella with:triple antigen tn:boostrix on:12/4/1999;
Goals
diabetes mellitus with:hba1c find:<6.5;
hypertension with:blood pressure find:<130/80;
Plans
diabetes mellitus with:Hba1c freq:1/12
sh]'

The following Doclescript output is derived by feeding the above sample SHEEP summary into the SHEEP parser:

OrderedCollection ('&ctx@admn[version],is[1.0]"&ctx@admn[auth-or],is[DrY K Oon]"&ctx@admn[date],is[12/8/2005]"&ctx@admn[admn@surname],is[Oon]"&ctx@admn[admn@firstName],is[Yeong]"&ctx@admn[birt-hday],is[18/7/59]"&ctx@allg[penicillin],to[shock@anaphylaxis]"&ctx@allg[eryt-hromycin],to [urti-caria]"&ctx@adr[metformin],to[diarrhea]"&ctx@eval [diabetesMellitus],in[1987]"&ctx@eval[hyperTension],in [2001]"&ctx@eval[deepVenousThrombosis],in [1997]"&ctx@eval[cough],for[2/12]"&ctx@eval [fracture.femur],ctx[right,comp-lication,open]"&ctx@eval [tuberculosis]"&ctx@eval [immunisation@travel@overSeas], ctx[viet-nam,thai-land,indi-a]"&ctx@eval[chest@pain],ctx[undiagnosed]"&ctx@risk@of[ischemicHeartDisease],ctx[high],from [problem@smoking,obesity]"&ctx@risk@of [carcinoma.colon],ctx[high],from[poly-posis.colon, &ctx@fh]"&ctx@phx[surgery.appendix@extirpation],in [1988]"&ctx@plan@for[injury.brain],ctx [motorCarAccident],in [2001]"&ctx@fh[carcinoma.colon],ctx[moth-er]"&ctx@fh[ischemicHeartDisease],ctx[father]"&ctx@fh[poly-posis.colon],ctx[brother]"&ctx@sh [sh@electrician],ctx[sh@selfEmployed]"&ctx@rxd [gliclazide],tn[diamicron mr], dose[30 mg],qty[1],freq[12/24],for[diabetesMellitus]"&ctx@rxd[atorvastatin],tn

[lipitor],dose[20 mg],qty[1],freq[1/7],for [hyper@cholesterol]''&ctx@immx[infection<clostridium@teta-ni],with[vaccine@clostridium@teta-ni],tn[tetToxBrand],on[12/7/1998]'‘&ctx@imm× [infection<measlesVirus&infection<mumpsVirus&infection <rubellaVirus],with[vaccinegbord-etella@pertussis&vaccine@clostridium@teta-ni&vaccine@diph-theriae],tn[boostrix],on[12/4/1999]'‘&ctx@goal@for[diabetesMellitus],with[hemoGlobin@glycated],find[<6.5] '‘&ctx@goal@for[hyperTension],with[bp], find[<130/80] '‘&ctx@plan@for[diabetesMellitus],with [hemoGlobin@glycated],freq[1/12]')

Sample SHEEP messages to invoke programmatic actions at the receiving end:

Command to backup the database

[sh stub backup sh]

Command to email summary to Docle@compuserve.com

[sh stub email summary of: patientId to: Docle@compuserve.com user: username password: password sh]

SHEEP and exchange patterns

SHEEP stands for simple health electronic exchange can also mean "stilted health expressions exchange patterns". SHEEP is powerful because its leverage is based on the "lowest common denominator" of health communication which is the English natural language. This results in non-specification and the non-reliance on any health coding systems or electronic record architectures.

In this invention, there is no premature rush to optimise the messaging contents by using any of the specified coding systems such as ICD (WHO International Coding Disease), Docle, Read, Snomed, LOINC or ICPC. In fact the introduction of medical codes inside medical messaging is the start down the slippery slope of incompatibility. This invention comprises means for ultimate generation of standalone canonical codes, hence coded information can flow, thereby achieving system interoperability and seamless health connectivity amongst a plurality of medical establishments that use a plurality of medical coding systems, a plurality of messaging protocols, a plurality of electronic health record architecture, a plurality of operating systems and a plurality of medical software application platforms for management of health data. This invention is based on the generic medical proposition model of health messaging and the system and method of parsing a natural language medical proposition into, but not limited to, one of its formal computer representations called Doclescript.

As will be clear to the skilled reader, the medical messaging system of the invention is interoperable, forward and backward compatible with all past, current or future health coding systems, health messaging protocols, electronic health record architectures, and software applications and platforms. In prior art systems, the assumption is that for syntactic and semantic interoperability, the sine qua non is a functionality involving the adoption of a standard health coding system, a standard electronic health record architecture, and a standard messaging protocol. The present invention dispenses with all these three criteria and yet achieve level 4 interoperability.

Modifications and improvements to the invention will be readily apparent to those skilled in the art after consideration of the above description and such modifications and improvements are intended to be within the scope which is defined by reference to the attached claims.

What is claimed is:

1. A system for electronically exchanging medical information, comprising:

an originating application accessing electronic medical records comprising data coded according to a first coding system;

a recipient application communicatively coupled to the originating application via a communications network, the recipient application accessing electronic medical records comprising data coded according to a second coding system;

input means associated with the recipient application for requesting an electronic medical record from the originating application;

first converter means associated with the originating application for converting the requested medical record to one or more medical information message structures, each of said message structures comprising an optional storyline keyword that sets the context for one or more subsequent statements, each of which statements comprise:

a genre selected from a set of genre keywords representing message categories;

a subject, comprising either a natural language string of one or more words or a nested statement; and optionally, one or more parametrized predicates comprising:

a context joiner selected from a set of context joiner keywords; and a parameter comprising a natural language string of one or more words or a nested statement;

means for communicating the messages to the recipient application; and second converter means associated with the recipient application for converting the messages into an electronic medical record comprising data coded according to said second coding system.

2. A method for exchanging medical information between an originating application and a recipient application, the method comprising converting the data to be exchanged from the data format of the originating application into one or more medical information message structures, each of said message structures comprising an optional storyline keyword that sets the context for one or more subsequent statements, each of which statements comprises:

a genre selected from a set of genre keywords representing message categories;

a subject, comprising either a natural language string of one or more words or a nested statement; and optionally, one or more parametrized predicates comprising:

a context joiner selected from a set of context joiner keywords; and a parameter comprising a natural language string of one or more words or a nested statement, the method comprising the steps of:

marshalling of stored data to be exchanged from the data format of the originating application into one or a series of propositions in stored memory;

carrying out a preliminary mapping step of each proposition to a designated empty cast comprising of a genre pragmas notated in natural language and a series of conjunctive pragmas notated in natural language;

instantiating the empty cast with the message contents by the mapping of medical codes and message content of the proposition into natural language equivalents;

inserting said natural language proposition equivalents into the empty cast by inserting subject content of the proposition into a space between a genre pragma and a first conjunctive pragma, and inserting clausal content of the proposition into associated conjunctive pragmas, so as to return a human and computer readable health proposition;

batching a plurality of said health propositions into a message cascade to eliminate repeating a pragma common genre pragma with multiple propositions, so to produce a human-and computer-readable medical message;

cuing said message cascade by designated begin and end pragmas, to provide the required medical information message structure.

3. A method according to claim 2, wherein the genre of each statement is either a medical information message or an administrative information message.

4. A method according to claim 2, wherein the context joiner of each statement is selected from the group of: a location descriptor, a temporal descriptor, a grammatical descriptor, an imperative descriptor, and a logical descriptor.

5. A method according to claim 2, further comprising the steps of:

communicating the messages to the recipient application; and converting the messages to the data format of the recipient application.

6. A method according to claim 5, wherein the step of communicating includes the step of cascading messages with common genres so as to delete duplicate genres.

7. A method according to claim 5, wherein the step of converting includes the steps of:

converting the data to be exchanged into an intermediate unitary health language; and converting the intermediate unitary health language into medical information messages.

8. A method according to claim 7, wherein the intermediate unitary health language is Doclescript.

9. A method according to claim 5, wherein the data format of either the originating application or the recipient application is selected from the group of: ICD, Docle, Read, ICPC, LOINC, or Snomed.

* * * * *